(12) United States Patent
Oda

(10) Patent No.: US 6,534,659 B2
(45) Date of Patent: Mar. 18, 2003

(54) SUFIDOMAIDOCARBOXYLIC ACIDS, METHOD FOR PRODUCTION THEREOF, AND USE THEREFOR

(75) Inventor: Yoshihisa Oda, Nara (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/840,402

(22) Filed: Apr. 23, 2001

(65) Prior Publication Data

US 2001/0047096 A1 Nov. 29, 2001

(30) Foreign Application Priority Data

Apr. 28, 2000 (JP) .......................... 2000-131272
Dec. 14, 2000 (JP) .......................... 2000-380868

(51) Int. Cl.$^7$ ............................................ C07D 277/04
(52) U.S. Cl. ........................................ 548/200; 252/391
(58) Field of Search ........................... 548/200; 252/391

(56) References Cited

U.S. PATENT DOCUMENTS 4,775,676 A * 10/1988 Chiesi ........................ 514/365

FOREIGN PATENT DOCUMENTS

| EP | 0 222 371 A2 | 5/1987 | ......... C07D/277/04 |
| GB | 2 098 215 A | 11/1982 | ......... C07D/277/04 |
| JP | 3-5469 | 1/1991 | ......... C07D/277/04 |
| JP | 10-140379 | 5/1998 | ............ C23G/1/06 |

OTHER PUBLICATIONS

Scuri et al., "Nesostiene: A New Mucoregulatory Agent", Chemical Abstracts, vol. 105, No. 19, Nov. 10, 1986, Columbus, Ohio, US, abstract No. 164771, XP-002172588.

* cited by examiner

Primary Examiner—Robert Gerstl
(74) Attorney, Agent, or Firm—Fish & Richardson P.C.

(57) ABSTRACT

Novel sulfidoamidocarboxylic acids (salts), a method for the production thereof, and uses therefor are provided. Sulfidoamidocarboxylic acids (salt) with a thiazolidine residue such as dimethylthiazolidine or methylthiazolidine or thiazolidine residue (residues), or a polycarboxylic acid (salt) residue such as dicarboboxylic acid (salt) or tricarboxylic acid (salt) or tetracarboxylic acid (salt) residue, a method for the production thereof, and uses therefor are also provided.

12 Claims, No Drawings

SUFIDOMAIDOCARBOXYLIC ACIDS, METHOD FOR PRODUCTION THEREOF, AND USE THEREFOR

BACKGROUND OF THE INVENTION

1. Field of the Invention

This invention relates to sulfidoamidocarboxylic acids, a method for the production thereof, and uses therefor. More particularly, it relates to sulfidoamidocarboxylic acids, a method for the production thereof, and a corrosion inhibitor for metals, a composition comprising a sulfidoamidocarboxylic acid and a polyamine, a salt formed by the reaction of a sulfidoamidocarboxylic acid with a polyamine, and a corrosion inhibitor for metals containing the composition and/or the salt.

2. Description of the Related Art

When water is used as a working medium, the water exerts various effects on the metal. One of the effects is corrosion of metals. The corrosion of metals is an important problem in the maintenance and management of various facilities and devices that handle aqueous media. For this problem, corrosion inhibitors for metals are generally used.

The corrosion inhibitors for metals are known in numerous kinds including inorganic inhibitors such as chromates and phosphates and organic inhibitors such as alkyl amines and alkyl ammoniums. They are useful under specific conditions.

SUMMARY OF THE INVENTION

By situation of application, corrosion inhibitors for metals are used in two modes, i.e., closed system and open system. The use in the open system is particularly important because it directly relates to the environmental conservation. There are some cases when the chromates may possibly prove problematic in safety and the phosphates in eutrophication of the aqueous environment. Most alkyl amines and alkyl ammoniums manifest relatively high toxicity. From the viewpoint of protecting the environment, it is important to develop corrosion inhibitors for metals that enjoys high safety because of low toxicity, exerts only a small load on the environment, and proves highly effective.

I have found that low molecular weight sulfidoamines such as dimethylthiazolidine have an effect of corrosion inhibition for metals. When these amines do not call for gasifiability, there is a limit to use because of strong odor.

Except for the problem of the toxicity, the organic corrosion inhibitors, which are liable to decompose relatively easily in the natural environment, are attractive. The alkyl amines and the alkyl ammoniums exhibit toxicity. A cause for the toxicity is considered to have the nature of cationic soap, since this inference is supported by that the fatty acids (salts) having hydrocarbon groups of an equal size generally exhibit low toxicity. Since the fatty acids (salts) are surfactants, they generally do not seem to be used by themselves as a corrosion inhibitor for metals though are utilized as a component for corrosion inhibitors for metals.

Most fatty acids (salts) generally exhibit low toxicity as compared with the corresponding amines and ammoniums. An effort to improve their effects on corrosion inhibition and heightening the manifestation speed of such effects, constitute themselves important tasks for the development of corrosion inhibitors for metals expected to be low toxicity. Since the task of heightening the effect of corrosion inhibition automatically entails a decrease in the amount of an inhibitor to be used, it has an important significance in decreasing the load to be exerted on the environment.

When such a fatty acid (salt) is modified in molecular structure and consequently enabled to increase the effect of corrosion inhibition for metals, it is thought to provide a corrosion inhibitor for metals of low toxicity. Further, this fatty acid can be expected to exhibit high biodegradability when a partial structure liable to be decomposed with an enzyme is incorporated into the molecular structure.

On the basis of this theory, I have taken notice of carboxylic acids (salts) with an amide bond (amide bonds) in the molecular structures thereof. Such carboxylic acids with the amide bond can be expected to subject to hydrolysis caused by the amidases of microorganisms.

I have performed a study on sulfidoamidocarboxylic acids (salts) and have consequently found that the sulfidoamidocarboxylic acids (salts), i.e. the derivatives of dimethylthiazolidine, manifest an excellent effect of corrosion inhibition for metals. Moreover, these sulfidoamidocarboxylic acids (salts) emit only weak odor as compared with low molecular weight sulfidoamines such as dimethylthiazolidine (DMT) that generally entail the problem of emitting strong odor. It has been found by this study that sulfidoamidocarboxylic acids (salts) are useful as a corrosion inhibitor for metals. This invention has been perfected as a result.

It is an object of this invention to provide novel sulfidoamidocarboxylic acids (salts), a method for the production thereof, and uses therefor.

This invention concerns sulfidoamidocarboxylic acids (salts) represented by the formula I:

(I)

wherein CnHm and Cn'Hm' denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to 2i+2–k–z, k for an integer of 1–5, and z for an integer of 1–5, and M represents a hydrogen atom or a metal atom or an ammonium, i.e. an ammonium originating in NH$_3$ or amines.

This invention also concerns a method for the production of sulfidoamidocarboxylic acids (salts) represented by the formula:

(I)

wherein CnHm and Cn'Hm' denote independently a hydrocarbon chain, CiHj denotes a hydrocarbon chain, n stands for an integer of 1–12, m for an integer of 2 to 2n, n' for an integer of to 1–15, m' for an integer of 2 to 2n', i for an integer of 2–20, j for an integer of 0 to 2i+2–k–z, k for an integer of 1–5, and z for an integer of 1–5, and M represents a hydrogen atom or a metal atom or an ammonium, i.e. an ammonium originating in NH$_3$ or amines, characterized by causing a sulfidoamine to react with an acid anhydride.

Further, this invention relates to a corrosion inhibitor for metals containing a sulfidoamidocarboxylic acid (salt) mentioned above.

In the following description, the group of compounds represented by the formula (I) will be referred to as "sulfidoamidocarboxylic acids (salts)."

Though the sulfidoamidocarboxylic acid (salt) indeed manifests a high effect on corrosion inhibition for metals even at a low concentration, the speed of manifestion of the corrosion inhibition does not necessary deserve such a designation as "very high". On use in the circumstance, it is desirable to increase the speed at manifestion of corrosion inhibition without decreasing the maximal level of corrosion inhibition observed in the sulfidocarboxylic acid (salt). I have made a diligent study in search of a method for using sulfidocarboxylic acid (salt).

Polyethyleneimine effectively functions as a corrosion inhibitor in a bath for acid washing metal materials (JP-A-10-140379), and I have made a study on this action thereof in detail. As a result, I have found that this compound, when used at a low concentration in a neutral or weakly acidic aqueous medium, promotes the effect of sulfidoamidocarboxylic acids (salts) on corrosion inhibition for metals. The result means polyethyleneimine functioned as synergy for corrsion inhibition for metals.

I have made a diligent study in search of a method for using sulfidoamidocarboxylic acid (salt). This invention has been perfected as a result. A theory has prevailed that when the polyamine and the sulfidoamidocarboxylic acid (salt) independently functioned, their coexistance brings an effect that is the sum of their respective characteristic properties. From their respective characteristic properties, it has been impossible to infer the effect that forms the essence of this invention, i.e. the fact that their coexistence greatly increases the speed of manifestation of corrosion inhibition for metals.

This invention provides a novel composition for inhibiting corrosion of metals. The present invention concerns the following compositions.

[1] A composition containing polyamine (salt) and a sulfidoamidocarboxylic acid (salt) represented by the formula (I):

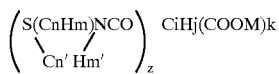

wherein CnHm and Cn'Hm' denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to 2i+2−k−z, k for an integer of 1–5, and z for an integer of 1–5, and M represents a hydrogen atom or a metal atom or an ammonium, i.e. an ammonium originating in $NH_3$ or amines.

[2] A salt obtained from the reaction of a polyamine (salt) with a sulfidoamidocarboxylic acid (salt) represented by the formula:

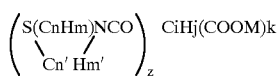

wherein CnHm and Cn'Hm' denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to 2i+2−k−z, k for an integer of 1–5, and z for an integer of 1–5, and M represents a hydrogen atom or a metal atom or an ammonium, i.e. an ammonium originating in $NH_3$ or amines.

[3] A composition for a corrosion inhibitor for metals containing a composition recited in [1] above and/or a salt incited in [2] above.

As a modification to [1] through [3] shown herein, a method for the corrosion inhibition which is characterized by causing polyethyleneimine (salt) and a sulfidoamidocarboxylic acid (salt) to be simultaneous presence, i.e. causing the two compound to mix or react with each other at the site of application, may be conceivable.

According to this invention, a sulfidoamidocarboxylic acid or a salt thereof can be provided.

Further, according to this invention, a method for producing a sulfidoamidocarboxylic acid (salt) by causing sulfidoamine to react with an acid anhydride can be provided.

Corrosion of metals can be inhibited with a sulfidoamidocarboxylic acid (salt) with a thiazolidine residue such as dimethylthiazolidine residue, a methylthiazolidine residue, or thiazolidine residue.

The sulfidoamidocarboxylic acid is enabled, by the addition thereto of polyamine, to expedite the manifestation of speed of corrosion inhibition of metals.

The above and other objects, features and advantages of the present invention will become clear from the following description of the preferred embodiments.

DESCRIPTION OF THE PREFERRED EMBODIMENTS

Corrosion inhibitors for metals hereafter may be referred as corrosion inhibitors.

The sulfidoamidocarboxylic acids (salts) to be used in this invention are generally represented by the formula I:

In the formula I, CnHm and Cn'Hm' independently signify a hydrocarbon chain and CiHj signifies a hydrocarbon chain. The sulfidoamidocarboxylic acids generally manifest their effect at a low concentration. In consideration of the solubility in water, it is highly proper to set the number of carbon atoms, n, at an integer of 1–12, the number of carbon atoms, n', at an integer of 1–15, and the number of carbon atoms, i, at an integer of 2–20. As the number of hydrogen atoms, m is an integer of 2 to 2n, m' an integer of 2 to 2n', and j an integer of 2 to 2i+2−k−z and they respectively correspond to the numbers, n, n', and i, of carbon atoms. While k is generally an integer of 1–5 and z an integer of 1–5, k=1 and z=1, k=2 and z=1, and k=2 and z=2, for example, are preferred choices of combinations. Particularly, k=1 and z=1 are frequently used. M signifies a hydrogen atom or a metal atom or ammonium, i.e. ammonium originating in $NH_3$ or amines. In the case of a sulfidoamidocarboxylate, the ammonium originating in polyethyleneimine is also embraced in the scope of M. In the case of a free sulfidoamidocarboxylic acid, M denotes hydrogen atom.

Examples of sulfidoamidocarboxylic acids represented by the formula I may include DMT-amic acids originating in dimethylthiazolidine such as DMT-succinamic acid (amic acid formed by the reaction of succinic anhydride with DMT (dimethyl thiazolidine)), DMT-maleamic acid (amic acid formed by the reaction of maleic anhydride with DMT), DMT-phthalamic acid (amic acid formed by the reaction of phthalic anhydride with DMT), DMT-trimellitamic acid (amic acid formed by the reaction of trimellitic anhydride with DMT), DMT-pyromellitamic acid (amic acid formed by the reaction of pyromellitic dianhydride with DMT), DMT-mellitamic acid (amid acid formed by the reaction of mellitic trianhydride with DMT), DMT-hexahydrophthalamic acid (amic acid formed by the reaction of hexahydrophthalic anhydride with DMT), DMT-citraconamic acid (amic acid formed by the reaction of citrononic anhydride with DMT), DMT-itaconamic acid (amic acid formed by the reaction of itaconic anhydride with DMT), DMT-naphthalenedicarboxylamic acid (amic acid formed by the reaction of naphthalenedicarboxylic anhydride with DMT), amic acid formed by the reaction of maleated methyl cyclohexene tetracarboxylic dianhydride with DMT, DMT-endomethylenetetrahydrophthalamic acid (amic acid formed by the reaction of endomethylenetetrahydrophthalic anhydride with DMT), DMT-chlorendoamic acid (amic acid formed by the reaction of chlorendic anhydride with DMT), DMT-methylendomethylenetetrahydrophthalamic acid (amic acid formed by the reaction of methylendomethylenetetrahydrophthalic anhydride with DMT), DMT-methyltetrahydrophthalamic acid (amic acid formed by the reaction of methyltetrahydrophthalic anhydride with DMT), amic acid formed by the reaction of methylnorbornene-2,3-dicarboxylic anhydride with DMT, DMT-tetrahydrophthalamic acid (amic acid formed by the reaction of tetrahydrophthalic anhydride with DMT), amic acid formed by the reaction of cyclopentanetetracarboxylic anhydride with DMT, amic acid formed by the reaction of glutaric anhydride with DMT, DMT-dodecenylsuccinamic acid (amic acid formed by the reaction of dodecenylsuccinic anhydride with DMT), and DMT-hexahydromethylphthalamic acid (amic acid formed by the reaction of hexahydromethylphthalic anhydride with DMT);

MT-amic acids originating in methylthiazolidine such as MT-succinamic acid (amic acid formed by the reaction of succinic anhydride with MT (methylthiazolidine)), MT-maleamic acid (amic acid formed by the reaction of maleic anhydride with MT), MT-phthalamic acid (amic acid formed by the reaction of phthalic anhydride with MT), MT-trimellitamic acid (amic acid formed by the reaction of trimellitic anhydride with MT), MT-pyromellitamic acid (amic acid formed by the reaction of pyromellitic dianhydride with MT), MT-mellitamic acid (amic acid formed by the reaction of mellitic trianhydride with MT), MT-hexahydrophthalamic acid (amic acid formed by the reaction of hexahydrophthalic anhydride with MT), MT-citraconamic acid (amic acid formed by the reaction of citraconic anhydride with MT), MT-itaconamic acid (amic acid formed by the reaction of itaconic anhydride with MT), MT-naphthalenedicarboxylamic acid (amic acid formed by the reaction of naphthalenedicarboxylic anhydride with MT), amic acid formed by the reaction of maleated methylcyclohexanetetracarboxylic dianhydride with MT, MT-endomethylenetetrahydrophthalamic acid (amic acid formed by the reaction of endomethylenetetrahydrophthalic anhydride with MT), MT-chlorendamic acid (amic acid formed by the reaction of chlorendic anhydride with MT), MT-methylendomethylenetetrahydrophthalamic acid (amic acid formed by the reaction of methylendomethylenetetrahydrophthalic anhydride with MT), MT-methyltetrahydrophthalamic acid (amic acid formed by the reaction of methylendomethylenetetrahydrophthalic anhydride with MT), MT-methyltetrahydrophthalamic acid (amic acid formed by the reaction of methyltetrahydrophthalic anhydride with MT), amic acid formed by the reaction of methylnorbornene-2,3-dicarboxylic anhydride with MT, MT-tetrahydrophthalamic acid (amic acid formed by the reaction of tetrahydrophthalic anhydride with MT), amic acid formed by the reaction of cyclopentanetetracarboxylic dianhydride with MT, amic acid formed by the reaction of glutaric anhydride with MT, MT-dodecenylsuccinamic acid (amic acid formed by the reaction of dodecenylsuccinic anhydride with MT), and MT-hexahydromethylphthalamic acid (amic acid formed by the reaction of hexahydromethylphthalic anhydride with MT); and T-amic acids originating in thiazolidine such as T-succinamic acid (amic acid formed by the reaction of succinic anhydride with T (thiazolidine)), T-maleamic acid (amic acid formed by the reaction of maleic anhydride with T), T-phthalamic acid (amic acid formed by the reaction of phthalic anhydride with T), T-trimellitamic acid (amic acid formed by the reaction of trimellitic anhydride with T), T-pyromelltamic acid (amic acid formed by the reaction of pyromellitic dianhydride with T), T-mellitamic acid (amic acid formed by the reaction of mellitic trianhydride with T), T-hexahydrophthalamic acid (amic acid formed by the reaction of hexahydrophthalic anhydride with T), T-citraconamic acid (amic acid formed by the reaction of citraconic anhydride with T), T-itaconamic acid (amic acid formed by the reaction of itaconic anhydride with T), T-naphthalenedicarboxylamic acid (amic acid formed by the reaction of naphthalenedicarboxylic anhydride with T), amic acid formed by the reaction of maleated methylcyclohexenetetracarboxylic dianhydride with T, T-endomethylenetetrahydrophthalamic acid (amic acid formed by the reaction of endomethylenetetrahydrophthalic anhydride with T), T-chlorendamic acid (amic acid formed by the reaction of chlorendic anhydride with T), T-methylendomethylenetetrahydrophthalamic acid (amic acid formed by the reaction of methylendomethylenetetrahydrophthalic anhydride with T), T-methyltetrahydrophthalamic acid (amic acid formed by the reaction of methyltetrahydrophthalic anhydride with T), amic acid formed by the reaction of methylnorbornene-2,3-dicarboxylic anhydride with T, T-tetrahydrophthalamic acid (amic acid formed by the reaction of tetrahydrophthalic anhydride with T), amic acid formed by the reaction of cyclopentanetetracarbocylic dianhydride with T, amic acid formed by the reaction of glutaric anhydride with T, T-dodecenylsuccinamic acid (amic acid formed by the reaction of dodecenylsuccinic anhydride with T), and T-hexahydromethylphthalamic acid (amic acid formed by the reaction of hexahydromethylphthalic anhydride with T).

Among other sulfidoamidocarboxylic acids enumerated above, DMT-succinamic acid, DMT-maleamic acid, DMT-phthalamic acid, DMT-trimellitamic acid, DMT-hexahydrophthalamic acid, and DMT-dodecenylsuccinamic acid are particularly preferred.

The sulfidoamidocarboxylic acids (salts) contemplated by this invention correspond to the compounds which result from partially amidating aliphatic or aromatic carboxylic acids possessing not less than two carboxyl groups in the molecular unit thereof (referred to in this invention as "polycarboxylic acids") with sulfidoamine. The sulfidoamidocarboxylic acids (salts) of this invention, therefore, are synthesized by a method which comprises subjecting a polycarboxylic acid and sulfidoamine to dehydrating condensation or causing a sulfidoamine to react with a chloride or an ester or anhydride of a polycarboxylic acid, for example.

In these methods, the method which comprising causing sulfidoamine to react with the intramolecular anhydride (with within the molecular unit a cyclic structure allowing the presence of —CO—O—CO—) of polycarboxylic acid proves particularly preferable. The reason for this preference is that the reaction is not only allowed to proceed without readily generation of by-products but also enabled, by controlling the reaction temperature, to proceed in the absence of solvents.

The acid anhydrides, which serve as raw materials for synthesis of sulfidoamidocarboxylic acids (salts), may include the following compounds: Succinic anhydride, maleic anhydride, phthalic anhydride, trimellitic anhydride, pyromellitic dianhydride, mellitic anhydride, cyclohexanedicarboxylic anhydride, citraconic anhydride, itaconic anhydride, naphthalenedicarboxylic anhydride, maleated methylcyclohexanetetracarboxylic dianhydride, endomethylenetetrahydrophthalic anhydride (norbornene-endo-2,3-dicarboxylic anhydride), chlorendic anhydride, methylendomethylenetetrahydrophthalic anhydride, methyltetrahydrophthalic anhydride, methylnorbornene-2,3-dicarboxylic anhydride, tetrahydrophthalic anhydride, cyclopentanetetracarboxylic dianhydride, glutaric anhydride, dodecenylsuccinic anhydride, and hexahydromethylphthalic anhydride.

Among other acid anhydrides enumerated above, phthalic anhydride, trimellitic anhydride, pyromellitic dianhydride, naphthalenedicarboxylic anhydride, cyclohexanedicarboxylic anhydride, succinic anhydride, maleic anhydride, and dodecenylsuccinic anhydride prove favorable and succinic anhydride, maleic anhydride, phthalic anhydride, and trimellitic anhydride prove particularly favorable in respect that they allow easy production of acid anhydrides. By causing these anhydrides to react with a sulfidoamine, sulfidoamidocarboxylic acids, such as succinamic acid, maleamic acid, phthalamic acid, and trimellitamic acid are synthesized easily.

If the number of carbon atoms of an acid anhydride to be used is unduly large, the excess generally will entail the disadvantage in that the solubility of the consequently formed sulfidoamidocarboxylic acid (salt) decreases. In consideration of the water solubility of the sulfidoamidocarboxylic acid or the dispersibility thereof in water, it is inferred that the number of carbon atoms in the polycarboxylic acid residue has the upper limit thereof in the proximity of 22. Though the lower limit of the number of carbon atoms ought to be theoretically allowed to fall as far down as 2, it is appropriately not less than 4 in consideration of the feasibility of the synthesis. The sulfidoamidocarboxylic acid (salt) with cyclohexanedicarboxylic acid residue has a greater ability to inhibit corrosion than that of the sulfidoamidocarboxylic acid (salt) with succinic acid residue. This result implies that the number of carbon atoms is preferred to be greater than a certain degree. Thus, for this invention, the number of carbon atoms i in the formula (I) is preferred to be not less than 5. The proper number of carbon atoms shown here pertains mainly to saturated aliphatic polycarboxylic acid residues and embraces such favorable exceptions as maleic acid residues, which are unsaturated polycarboxylic acid residues.

For the corrosion inhibitors containing a compound represented by the formula I, it is appropriate that i stands for an integer of 2–20, preferably an integer 3–14, j for an integer of 0 to 2i+2-k-z, k for an integer of 1–5, z for an integer of 1–5, and M for a hydrogen atom, a metal atom, or ammonium as mentioned above. Examples of the metal atom mentioned above may include alkali metal atom and alkaline earth metal atom. Among other metal atom mentioned above, alkali metal atom proves favorable and lithium, sodium, and potassium prove particularly favorable. When a divalent or trivalent metal atom is used as a metal atom M, half of the atom of divalent metal, $Mg_{1/2}$, $Ca_{1/2}$, $Sr_{1/2}$, $Ba_{1/2}$, $Zn_{1/2}$, $Cu_{1/2}$, $Fe_{1/2}$ for example, or one-third of the atom of trivalent metal, $Al_{1/3}$, $Fe_{1/3}$, $La_{1/3}$, $Ce_{1/3}$ for example, is equivalent to M.

The hydrocarbon chains, —CnHm— and —Cn'Hm'—, which are in the sulfidoamidocarboxylic acids (salts) of this invention, are generally aliphatic hydrocarbon chains with a linear or branched chain structure. The hydrocarbon chains with an aromatic ring or an aromatic cyclic structure are also usable, depending on the purpose for which the relevant acids are used. If the hydrocarbon chains, —CnHm— and —Cn'Hm'—, are unduly large, they will be at a disadvantage that the water solubility of the sulfidoamidocarboxylic acids (salts) or the dispersibility thereof in water decreases. In consideration of the stability of sulfidoamidocarboxylic acids (salts), it is advantageous for the hydrocarbon chains, —CnHm— and —Cn'Hm'—, that n denotes an integer of 1–12, m an integer of 2 to 2n, n' an integer of 1–15, and m' an integer of 2 to 2n'.

As concrete examples of the sulfidoamidocarboxylic acids (salts) of this invention, thiazolidine residues such as dimethylthiazolidine, methylthiazolidine, and thiazolidine residues and polycarboxylic acid (salt) residues such as dicarboxylic acid (salt), tricarboxylic acid (salt), and tetracarboxylic acid (salt) residues have already been cited.

As the raw materials for the synthesis of such sulfidoamidocarboxylic acids, thiazolidines are advantageously used.

The thiazolidines and the thiazolidine residues have a five-membered cyclic structure including a nitrogen atom and a sulfur atom. In this case, the minimum numbers of n and n' are 2 and 1 respectively. Also in this case, the condition that n is an integer of 1–12, m an integer of 2 to 2n, n' an integer of 1–15, and m' an integer of 2 to 2n' is satisfied. In the 2,2-dimethylthiazolidine, which is used particularly preferably in this invention, CnHm is $C_2H_4$ and Cn'Hm' is $C_3H_6$.

The compounds analogous to thiazolidines may be designated by using —CRR'— instead of —Cn'Hm'— (as shown in the formula II). In this case, the groups R and R' independently denote a hydrogen atom or a hydrocarbon group. Their sizes are preferred to be equivalent approximately to not more than 12 carbon atoms. More preferably, the total carbon atoms in these two groups are not more than 12.

(II)

As particularly preferred sulfidoamine residues, dimethylthiazolidine residues (hereinafter abbreviated as R, R'=$CH_3$, DMT—), methylthiazolidine residues (hereinafter abbreviated as R=$CH_3$, R'=H, MT—), and thiazolidine residues (hereinafter abbreviated as R, R'=H, T—) may be cited.

As other sulfidoamine residues, thiomorpholine residues, thiomorpholines residues with structures originating respectively in thiomorpholine and thiomorpholines are hopeful.

The number of the sulfidoamine residues is decided in accordance with the acid anhydride to be used for the synthesis. In consideration of performance in use or industrial utilizability, the number is preferred to be in the range of 1–5. In the sulfidoamidocarboxylic acids (salts), z is preferred in the range of 1–5.

The amounts of an acid anhydride and a sulfidoamine to be used in their reaction are generally such that the equivalent ratio of the partial structure, —CO—O—CO—, in the acid anhydride to the sulfidoamine is generally in the range of 1–3:3–1, preferably in the range of 1–1.5: 1.5–1, and especially 1:1. The term "equivalent ratio 1:1" as used herein designates 1:1 (molar ratio) in the case of the reaction of a monoanhydride such as succinic anhydride, maleic anhydride, phthalic anhydride, or trimellitic anhydride with thiazolidine, methylthiazolidine, or dimethylthiazolidine, 1:2 (molar ratio) where the acid anhydride is a dianhydride such as pyrollitic dianhydride, or 1:3 (molar ratio) where the acid anhydride is a trianhydride such as mellitic trianhydride.

In this invention, it is advantageous to use succinic anhydride, maleic anhydride, phthalic anhydride, or trimellitic anhydride as the acid anhydride and dimethylthiazolidine (available from Nippon Shokubai Co., Ltd.) as the sulfidoamine. When they are used for the reaction, it is particularly advantageous to use them at an equivalent ratio of 1:1 because this equivalent ratio allows warrants smooth progress of the relevant reaction. When the reaction between the acid anhydride and sulfidoamine (the reaction for forming an amide bond) proceeds smoothly, the product can be handled as a sulfidoamidocarboxylic acid without being further purified. As the corrosion inhibitor, i.e. the use contemplated by this invention, the product can be used as it is or after purification if necessary.

The reaction temperature between the acid anhydride and sulfidoamine is not particularly restricted but only required to be capable of inducing a reaction of the acid anhydride with sulfidoamine. It is generally in the range of below ice cooling (0° C.)–120° C., preferably in the range of 15–120° C.

The reaction duration between the acid anhydride and sulfidoamine, which terminates when the generation of the reaction heat ceases to be observed, is generally not less than two minutes, and preferably in the approximate range of 2–60 minutes. Prolonged reaction time may be needed depending on reaction temperature.

The reaction between the acid anhydride and sulfidoamine is carried out in the absence of a solvent or in the presence of a solvent. Examples of the solvent to be used for the reaction may include various organic solvents of ketones such as acetone and methyl ethyl ketone; ethers such as diethyl ether and dimethoxyethane; halogenated solvents such as dichloromethane and carbon tetrachloride; and hydrocarbons such as hexane, petroleum ether, ligroin, benzene, toluene, and xylene. Though the amount of such a solvent to be used is not particularly limited, it is properly 0–10 times, preferably 0–2 times (not inclusive of 0) the total amount of the raw materials used.

The reaction can be carried out generally in the atmosphere of an inert gas such as nitrogen or argon. When such a solvent as acetone is used in an amount of not less than 1 time the amount of the raw materials, the reaction can be carried out under the atmosphere of air because the vapor of the solvent is enabled to cover the surface of the reaction product at the temperature of heating under ambient atmospheric pressure. Even when small amount of solvent less than 1 time the amount of the raw material or no solvent is used, the reaction may be carried out under the atmosphere of air, depending on the conditions of the operation involved. Though the reaction pressure is not particularly limited, it may be ambient atmospheric pressure.

The sulfidoamidocarboxylic acid, which is formed by the reaction between an acid anhydride and a sulfidoamine, may be neutralized into a salt with an inorganic base or an organic base depending on the purpose of use. Here, the term "inorganic base" embraces substances similar to the inorganic base, and the term "organic base" embraces substances similar to the organic base. Examples of the inorganic bases and the substances similar to the inorganic bases may include lithium hydroxide, sodium hydroxide, potassium hydroxide, lithium carbonate, sodium carbonate, potassium carbonate, lithium hydrogen carbonate, sodium hydrogen carbonate, potassium hydrogen carbonate, ammonia, ammonium carbonate, and ammonium hydrogen carbonate. Depending on the condition under which the corrosion inhibitor is used, oxides, hydroxides, carbonates, or hydrogen carbonates of magnesium, calcium, and strontium, for example, may be also used as inorganic base. Examples of the organic bases and the substances similar to the organic bases may include alkylamines, dialkylamines, and trialkylamines such as ethanolamine, diethanolamine, triethanolamine, allylamine, diallylamine, methylamine, dimethylamine, trimethylamine, ethylamine, diethylamine, and triethylamine. As organic bases, dimethylthiazolidine, methylthiazolidine, thiazolidine, cysteamine, and polyamines which will be described more specifically herein below may be also used, depending on the purpose of use. The term "ammoniums" as used herein means amines such as have a hydrogen ion bonded thereto and ammonium ($NH_4$).

Composition of Polyamine (Salt) with Sulfidoamidocarboxylic Acid and Salts Obtained by the Reaction Thereof First of all, raw substances to be used in this invention will be described.

In this invention, various species of polyamine can be used. The term "polyamine" as used herein means "an organic compound including not less than two amino groups," preferably "an organic compound including not less than 10 amino groups on the average in the molecular unit thereof." The term "amino group" as used herein means —$NH_2$, —NH—, N (call for three monovalent coupling bonds) that have not formed an amide structure bond. As one example of the amino group, polyethyleneimine may be cited. The polyethyleneimine is a polyamine type polymer including (—$CH_2$—$CH_2$—NH—) as the monomer unit. Examples of the macromolecule including a nitrogen atom in the side-chain portion may include polyvinylamine (—$CH_2$—$CH(NH_2)$— as the monomer unit), polyallylamine (—$CH_2$—$CH(CH_2NH_2)$— as the monomer unit), etc. Besides, diamines such as $H_2N$—$(CH_2CH_2O)_x$—$NH_2$ (x=13 where the molecular weight is about 600) and $H_2N$—$(CH_2CH(CH_3)O)_x$—$NH_2$ (x=10 where the molecular weight is about 600) may be cited.

In the examples of this invention, polyethyleneimine (having a number average molecular weight of 70000, available from Nippon Shokubai Co., Ltd.) was preferentially used as the polyamine. As inferred from the function of polyethyleneimine, which will be discussed hereinafter, the use of polyvinylamine or polyallylamine can be expected to bring the same function or effect as the polyethyleneimine.

No particular restriction is originally imposed on the lower limit or the upper limit of the molecular weight of polyamine. When this molecular weight decreases to approximate closely to that of ethylenediamine or diethylenetriamine, it is considered that the polyamine will bring about the problem of toxicity. Thus, the molecular weight at which the polyamine is supposed to be difficult in passing a cell membrane, serves as the criterion for the lower limit of the molecular weight. It is generally held that in the case of a low molecular compound, the compound will cease easily passing a cell membrane when the molecular weight exceeds about 600. It is, therefore, allowed to set the lower limit of the molecular weight of polyamine at 600 as the standard. No restriction is originally imposed on the upper limit of the molecular weight so long as the compound has solubility in water and solubility in an organic solvent. As concrete examples of the commercially available polyamine, polyethyleneimine preferentially used in Examples 8–10 has a molecular weight in the neighborhood of 70,000 and polyallylamine a molecular weight in the approximate range of 10,000–100,000. In consideration of the proper range of molecular weight, it may be in the range of 0.0085–100 times, preferably 0.01–100 times, more preferably 0.1–10 times, the molecular weight of 70,000 as the center.

The salt of sulfidoamidocarboxylic acid with polyamine to be used in this invention is preferably obtained by the reaction of sulfidoamidocarboxylic acid with polyamine. This reaction is a simple neutralization reaction of a base and an acid which is induced by mixing the base and the acid. The reaction can be effected in the absence of a solvent or in the presence of water, an aqueous solvent, or an organic solvent. The reaction temperature is not particularly restricted but only required to be in a range in which the polyamine and the sulfidoamidocarboxylic acid are not decomposed. The reaction temperature for practical use is in the approximate range of 0 to 100° C., preferably in the approximate range of 0 to 50° C., and especially in the approximate range of 10 to 40° C. The ratio of the amounts of polyamine and sulfidoamidocarboxylic acid to be used for the reaction is 1:1 in equivalent ratio as the standard where the reaction forms a normal salt. It maybe in the range from 1:1 in equivalent ratio to 1:1 in molar ratio where the reaction forms a basic salt.

The polyamine is usually treated as a simple substance. It is not only an aggregate of macromolecules that differ in size as viewed on the molecular level, but also the reactivity of the existing amino groups is not uniform. In the synthesis of a salt of sulfidoamidocarboxylic acid with polyamine, it is one of the realistic choices to continue the reaction between the polyamine and the sulfidoamidocarboxylic acid by adding one of the reactants to the other, while sampling the reaction mixture, converting the sample into an aqueous solution, and then testing the aqueous solution for hydrogen ion concentration with a pH test paper or a pH meter. By this method, various salts or a mixture containing such salts manifesting acidity through basicity can be synthesized, and the degree of acidity or the degree of basicity can be selected depending on the purpose of use.

In consideration of the fact that in this invention a mixture of polyamine with a sulfidoamidocarboxylic acid can be used as a corrosion inhibitor for metals, the mixing ratio of the amounts of the polyamine and the sulfidoamidocarboxylic acid may be set in the range of 10:1 to 1:10, and even in the range of 300:1 to 1:000 in weight ratio. In this mixture, the salt is formed from a polyamine and a sulfidoamidocarboxylic acid.

In the formation of a salt of sulfidoamidocarboxylic acid with polyamine, it may be used a sulfidoamidocarboxylate instead of the sulfidoamidocarboxylic acid. Ammonium sulfidoamidocarboxylate, for example, is thought to react with the polyamine and liberate ammonia to form the salt of polyamine consequently. Alternatively, the salt may be formed by double decomposition. A metal salt of sulfidoamidocarboxylic acid such as sodium sulfidoamidocarboxylate, instead of a free acid, may be caused to react with a salt of polyamine instead of a polyamine, for example, a chloride salt or a sulfate salt.

The mixture of a polyamine with a sulfidoamidocarboxylic acid (salt) for use in this invention can be prepared by mixing these materials in the absence of solvents or in the presence of water, an aqueous solvent, or an organic solvent. Here, an aqueous solvent means a mixture of water and organic solvents such as aqueous methanol, aqueous ethanol, aqueous propanol, aqueous acetone, for example. Though the mixing ratio of these two materials is preferably selected in the range of 3:1 to 1:3 in weight ratio, it may be selected in the range of 10:1 to 1:10 and, depending on the conditions, may be selected in the range of 300:1 to 1:100.

The mixture of a salt of polyamine with a sulfidoamidocarboxylic acid can also be prepared in same manner.

The polyamine (salt) and the sulfidoamidocarboxylic acid (salt) can be easily mixed or caused to react with each other in water, an aqueous solvent or an organic solvent. For practical utilization of this invention, the method may be adopted which comprises simultaneously introducing the polyamine (salt) and the sulfidoamidocarboxylic acid (salt) to a given site of application, e.g., water, sea water and allowing them to coexist at the site, namely mixing them or allowing them to react with each other thereby inhibiting corrosion. The reason is that this method results in forming a composition and/or a salt of polyamine (salt) with the sulfidoamidocarboxylic acid (salt), though generally in the form of a dilute solution.

The corrosion inhibitor and the composition therefor contemplated by this invention are intended to inhibit corrosion by increasing the polarization resistance. They, therefore, can be applied not only to iron type metals such as iron and iron alloys, e.g., carbon steel and stainless steel but also to metals in general which can be expected to increase polarization resistance. Examples of the object for application may include copper and copper alloys such as brass and cupro-nickel, zinc and zinc alloys, magnesium and magnesium alloys, aluminum and aluminum alloys, nickel and nickel alloys, chromium and chromium alloys, and lead, tin, manganese, cobalt, molybdenum, tungsten, vanadium, and cadmium and the alloys thereof besides the iron type metals mentioned above.

The compound of this invention is a compound represented by the structural formula (I) mentioned above and is useful as a corrosion inhibitor for metals, for example.

The compound represented by the formula, which is analogous to the compound represented by the formula (I), may be used as a corrosion inhibitor for metals:

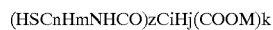

wherein n, m, i, j, z, k, and M have the same meanings as in the formula (I).

Examples of the compound represented by the formula mentioned above may include N-(mercaptoethyl) succinamic acid, N-(mercaptoethyl)maleamic acid, N-(mercaptoethyl)phthalamic acid, N-(mercaptoethyl) trimellitamic acid (dicarboxylic acid,i.e., k=2), N-(mercaptoethyl)dodecenylsuccunamic acid, N-(mercaptopropyl)succinamic acid, N-(mercaptopropyl) maleamic acid, N-(mercaptopropyl)trimellitamic acid (dicarboxylic acid), N-(mercaptopropyl) dodecenylsuccinamic acid, N-(mercaptophenyl)succinamic acid, N-(mercaptophenyl)maleamic acid, N-(mercaptophenyl)phthalamic acid, N-(mercaptophenyl) trimellitamic acid (dicarboxylic acid), N-(mercaptophenyl) dodecenylsuccinamic acid. These compounds are also useful as corrosion inhibitors for metals.

EXAMPLES

Now, this invention will be described specifically below with reference to examples. It should be noted, however, that this invention is not limited to these examples.

Example 1

At room temperature, 14.8 g (100 mmoles) of phthalic anhydride pulverized in advance by the use of a mortar and 11.7 g (100 mmoles) of 2,2-dimethylthiazolidine (available from Nippon Shokubai Co., Ltd.) were mixed. Then, the resultant mixture was heated at 100° C. for 10 minutes to melt the reactants and allow them to induce a reaction. Consequently, 26.4 g (100% in yield) of the reaction product was obtained. The $^1$H-NMR spectrum (in [$^2$H]chloroform under 200 MHz at δ ppm) of the reaction product is as follows: 1.97 (s, 6H, C(CH$_3$)$_3$), 2.88 (t, 2H, J=6.0 Hz, —CH$_2$—S—), 3.56 (t, 2H, J=6.0 Hz, —CH$_2$—N—), 7.28 (d, 1H, J=7.5 Hz), 7.43 (t, 1H, J=7.5 Hz), 7.59 (t, 1H, J=7.5 Hz), 8.06 (d, 1H, J=7.5 Hz), and 10.52 (bs, 1H, —COOH). The signal at 7.28–8.06 ppm could be assigned to the hydrogen atoms linked to the benzene ring. The reaction product, therefore, was identified to be N-(2-carboxybenzoyl)-2,2-dimethylthiazolidine represented by the formula (III), namely DMT-phthalamic acid:

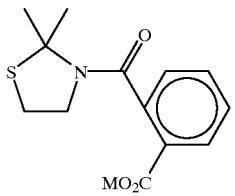

(III)

wherein M denotes hydrogen atom.

The reaction product was caused to react with sodium hydroxide at an equimolar ratio to form a sodium salt.

The resultant sodium salt was tested for rating the ability to inhibit corrosion. The value of Rp determined by the use of an iron electrode was 110 Ω in the absence of the addition and, subsequent to the addition, 210 Ω (ability to inhibit corrosion 47.6%) after the elapse of 20 minutes, 3000 Ω (ability to inhibit corrosion 96.3%) after the elapse of 15 hours, and thereafter the peak of about 7100 Ω (ability to inhibit corrosion 98.5%).

Example 2

At room temperature, 9.8 g (100 mmoles) of maleic anhydride and 11.73 g (100 mmoles) of 2,2-dimethylthiazolidine and 11.7 ml of acetone added thereto were mixed and allowed to induce a reaction. After the generation of heat ceased, the reaction product was analyzed in the same manner as in Example 1 and consequently identified as N-(2-carboxylvinylcarbonyl)-2,2-dimethylthiazolidine represented by the formula (IV):

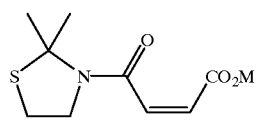

(IV)

wherein M denotes hydrogen atom.

The reaction product in the unrefined state and 10 ml of aqueous sodium hydroxide solution (containing 4.0 g, 100 mmoles, of NaOH) added thereto were mixed to obtain an aqueous solution of the sodium salt of a sulfidoamide derivative of maleic acid.

The resultant sodium salt was tested for rating the ability to inhibit corrosion. The value of Rp determined by the use of an iron electrode was 90 Ω in the absence of the addition and, subsequent to the addition, 200 Ω (ability to inhibit corrosion 55.0%) after the elapse of 20 minutes, 2000 Ω (ability to inhibit corrosion 95.5%) after the elapse of 15 hours, and thereafter the peak of about 4800 Ω (ability to inhibit corrosion 98.1%).

Example 3

At room temperature, 10.0 g (100 mmoles) of succinic anhydride and 11.73 g (100 mmoles) of 2,2-dimethylthiazolidine and 11.7 ml of acetone added thereto were mixed and allowed to induce a reaction. After the generation of heat ceased, the reaction product was analyzed in the same manner as in Example 1 and consequently identified as N-(2-carboxylethylcarbonyl)-2,2-dimethylthiazolidine represented by the formula (V):

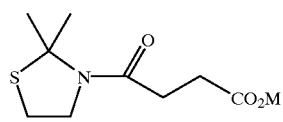

(V)

wherein M denotes hydrogen atom.

The reaction product in the unrefined state and 10 ml of aqueous sodium hydroxide solution (containing 4.0 g, 100 mmoles, of NaOH) added thereto were mixed to obtain an aqueous solution of the sodium salt of a sulfidoamide derivative of succinic anhydride.

The resultant sodium salt was tested for rating the ability to inhibit corrosion. The value of Rp determined by the use of an iron electrode was 80 Ω in the absence of the addition and, subsequent to the addition, 280 Ω (ability to inhibit corrosion 71.4%) after the elapse of 25 minutes, 3600 Ω (ability to inhibit corrosion 97.8%) after the elapse of 15 hours, and thereafter the peak of about 4160 Ω (ability to inhibit corrosion 98.1%).

Example 4

At room temperature, 7.71 g (50 mmoles) of cyclohexanedicarboxylic anhydride and 5.87 g (50 mmoles) of 2,2-dimethylthiazolidine and 5.9 ml of acetone added thereto were mixed. The resultant mixture was heated at 110° C. for 30 minutes to be melted and allowed to induce a reaction. The reaction product was analyzed in the same manner as in Example 1 and identified to be N-(2-carboxylcyclohexylcarbonyl)-2,2-dimethylthiazolidine represented by the formula (VI):

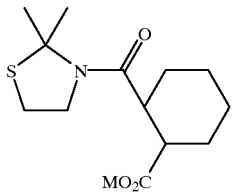

(VI)

wherein M denotes hydrogen atom.

The reaction product was cooled and then mixed in the unrefined state with 10 ml of aqueous sodium hydroxide solution (containing 2.0 g, 50 mmoles, of NaOH) to obtain an aqueous solution of sodium salt of a sulfidoamide derivative of cyclohexanedicarboxylic acid.

The resultant sodium salt was tested for rating the ability to inhibit corrosion. The value of Rp determined by the use of an iron electrode was 90 Ω in the absence of the addition and, subsequent to the addition, 640 Ω (ability to inhibit corrosion 95.9%) after the elapse of 20 minutes, 5300 Ω (ability to inhibit corrosion 98.3%) after the elapse of 15 hours, and thereafter the peak of about 7450 Ω (ability to inhibit corrosion 98.8%).

Example 5

At room temperature, 19.21 g (100 mmoles) of trimellitic anhydride and 11.73 g (100 mmoles) of 2,2-dimethylthiazolidine and 11.7 ml of acetone added thereto were mixed. The resultant mixture was heated at 110° C. for 30 minutes to be melted and allowed to induce a reaction. The reaction product was analyzed in the same manner as in Example 1 and identified to be a compound represented by the formula (VII):

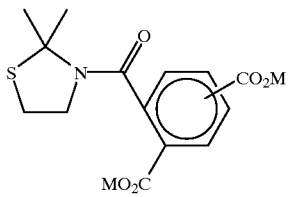

(VII)

wherein M denotes hydrogen atom.

The reaction product was cooled and then mixed in the unrefined state with 20 ml of aqueous sodium hydroxide solution (containing 8.0 g of NaOH) to obtain an aqueous solution of sodium salt of a sulfidoamide derivative of trimellitic acid.

The resultant sodium salt was tested for rating the ability to inhibit corrosion. The value of Rp determined by the use of an iron electrode was 120 Ω in the absence of the addition and, subsequent to the addition, 380 Ω (ability to inhibit corrosion 68.4%) after the elapse of 20 minutes, 3020 Ω (ability to inhibit corrosion 96.7%) after the elapse of 25 hours, and thereafter the peak of about 4020 Ω (ability to inhibit corrosion 97.5%).

Example 6

At room temperature, 5.45 g (25 mmoles) of pyromellitic anhydride and 5.87 g (50 mmoles) of dimethylthiazolidine and 5.9 ml of acetone added thereto were mixed. The resultant mixture was heated at 110° C. for 10 minutes to be melted and allowed to induce a reaction. The reaction product was analyzed in the same manner as in Example 1 and identified to be a compound represented by the formula (VIII):

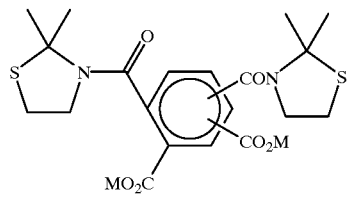

(VIII)

wherein M denotes hydrogen atom.

The reaction product was cooled and then mixed in the unrefined state with 10 ml of aqueous sodium hydroxide solution (containing 2.0 g of NaOH) to obtain an aqueous solution of sodium salt of a sulfidoamide derivative pyromellitic acid.

The resultant sodium salt was tested for rating the ability to inhibit corrosion. The value of Rp determined by the use of an iron electrode was 90 Ω in the absence of the addition and, subsequent to the addition, 490 Ω (ability to inhibit corrosion 81.6%) after the elapse of 20 minutes, 2230 Ω (ability to inhibit corrosion 96.0%) after the elapse of 15 hours, and thereafter the peak of about 2620 Ω (ability to inhibit corrosion 96.6%).

In the following examples, DMT-phthalamic acid (hereinafter abbreviated as DMT-Pht) and DMT-succinamic acid (hereinafter abbreviated as TMT-Scc) were used each as a sulfidoamidocarboxylic acid. Their chemical structures were as shown below. DMT-, Pht, and Scc denote 2,2-dimethylthiazolidine residue, phthalic acid residue, and succinic acid residue, respectively. In the examples, comparative examples, and referential example, polyethyleneimine (abbreviated as PEI) was used as polyamine.

DMT-Pht:

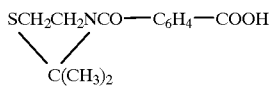

wherein —$C_6H_4$— denotes o-phenylene chain.

DMT-Scc:

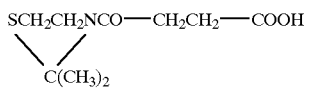

Example 7

To aqueous solution of PEI (1%), was gradually added DMT-Pht and allowed to induce a reaction. The pH of the reaction solution was tested with a pH test paper. The aqueous PEI solution had an original pH of 11 (minimum). This pH value gradually fell as the addition of DMT-Pht thereto advanced. At the time that the pH reached 7, the addition of DMT-Pht was ceased. Consequently, the PEI salt (aqueous solution) of DMT-Pht was obtained. The aqueous solution of the PEI salt of DMT-Pht could be concentrated and dried till hardness to produce a solid substance.

Example 8

The effect of corrosion inhibition on iron during their simultaneous use of PEI and DMT-Pht was tested by the method described in Referential Example. The results are shown in Tables 1 and 2.

Example 9

The effect of corrosion inhibition on low-carbon steel during their simultaneous use of PEI and DMT-Pht was tested by the method described in Referential Example. The results are shown in Tables 1 and 2.

Example 10

The effect of corrosion inhibition on iron during their simultaneous use of PEI and DMT-Scc was tested by the method described in Referential Example. The results are shown in Tables 1 and 2.

Example 11

This experiment was performed for the purpose of confirming the occurrence of an acid-base reaction.

To 133.5 mg of DMT-Pht dissolved in 5 ml of methanol, was added 22 mg of PEI (anhydrous product of a molecular weight of 10,000, available from Nippon Shokubai Co., Ltd. and sold under the product code "SP200") and allowed to induce a reaction. The resultant reaction mixture was concentrated under a stream of nitrogen gas. Clear resinous solid substance, 160.3 mg, was obtained.

The NMR spectrum (in [$^2$H]chloroform under 200 MHz at δ ppm) described 1.90 (bs, 6H), 2.83 (bs, 2–3H), and 3.53 (bs, 2H) and showed a complicated signal of a large width (6H) at 7.1–8.0. Incidentally, the numbers of carbon atoms in the spectrum of the reaction product shown herein were approximate numerical values found from the integral curve on the assumption that the signal at 1.90 ppm originated in $C(CH_3)_2$ because the signals had large width and were complicated.

The NMR spectrum of the DMT-Pht was as already described in Example 1. In the NMR spectrum (in [$^2$H] chloroform under 200 MHz at δ ppm) of polyethyleneimine, signals were found at 1.99 (bs, 1H, NH) and 2,5–2.8 (4H, $CH_2$). Thus, the formation of a salt by the chemical reaction was confirmed.

The presence of methanol in an amount of about 4.3 mg was confirmed by the NMR spectrum of this solid substance. The theoretical yield of the product containing 4.3 mg of methanol is calculated to be 159.8 mg. The found yield 160.3 mg and the calculated yield 159.8 mg may well be regarded as coinciding in consideration of the measurement error.

The NMR spectrum demonstrated that the PEI and the DMT-Pht reacted with each other. As regards the combination of components for the reaction mixture, the possibility of the reaction for forming an amide bond besides the acid-base reaction is not undeniable. It has been generally held, however, that the reaction of amidation induced by mixing a carboxylic acid with amine does not actually occur at room temperature and that once the reaction of amidation occurs, the formed water is removed and the loss of mass reaches 9.0 mg. Thus, it is concluded that the reaction of amidation did not actually occur. The formation of a salt from PEI and DMT-Pht by the operation of the present reaction was confirmed.

Comparative Example 1

The effect of DMT-Pht on corrosion of iron was assayed by the method described in Referential Example as set forth below. The results are shown in Tables 1 and 2.

Comparative Example 2

The effect of DMT-Pht on corrosion of low-carbon steel was assayed by the method described in Referential Example. The results are shown in Tables 1 and 2.

Comparative Example 3

The effect of DMT-Scc on corrosion of iron was assayed by the method described in Referential Example. The results are shown in Tables 1 and 2.

Comparative Example 4

The effect of PEI on corrosion of iron was assayed by the method described in Referential Example. The results are shown in Tables 1 and 2.

Comparative Example 5

The effect of PEI on corrosion of low-carbon steel was assayed by the method described in Referential Example. The results are shown in Tables 1 and 2.

TABLE 1

| | | | Rp (ohm) | | | |
|---|---|---|---|---|---|---|
| | Sample | Electrode | Sample not added | After 20 min. | After 15 hrs | Peak |
| Ex 8 | DMT-Pht + PEI | Fe | 90 | 800 | 6450 | 7000 |
| Ex 9 | DMT-Pht + PEI | X65 | 170 | 1030 | 3980 | 6650 |
| Ex 10 | DMT-Scc + PEI | Fe | 80 | 700 | 6150 | 11000 |
| Com. Ex 1 | DMT-Pht | Fe | 110 | 210 | 3000 | 7100 |
| Com. Ex 2 | DMT-Pht | X65 | 180 | 620 | 3380** | 6500 |
| Com. Ex 3 | DMT-Scc | Fe | 80 | 280* | 3600 | 4160 |
| Com. Ex 4 | PEI | Fe | 90 | 280 | 380 | 520 |
| Com. Ex 5 | PEI | X65 | 170 | 430 | 760 | 1220 |

EX: Example,
Com. Ex: Comparative Example
*After 25 minutes
**After 20 hours
Sample not added: Before addition of sample

TABLE 2

| | | | Ability to inhibit corrosion (%) | | |
|---|---|---|---|---|---|
| | Sample | Electrode | Sample not added | After 20 min. | After 15 hrs | Peak |
| Ex 8 | DMT-Pht + PEI | Fe | — | 88.8 | 98.6 | 98.7 |
| Ex 9 | DMT-Pht + PEI | X65 | — | 83.5 | 95.9 | 97.3 |
| Ex 10 | DMT-Scc + PEI | Fe | — | 88.6 | 98.7 | 99.3 |
| Com. Ex 1 | DMT-Pht | Fe | — | 48 | 96.3 | 98.5 |
| Com. Ex 2 | DMT-Pht | X65 | — | 71.0 | 94.7 | 97.2 |
| Com. Ex 3 | DMT-Scc | Fe | — | 71.4 | 97.8 | 98.1 |
| Com. Ex 4 | PEI | Fe | — | 67.9 | 76.3 | 82.7 |
| Com. Ex 5 | PEI | X65 | — | 60.5 | 77.6 | 86.1 |

Referential Example

The ability to inhibit corrosion was assayed by determination of polarization resistance (Faraday resistance, Rp). In this determination, cylindrical iron electrodes (9.5 mm in diameter and 12.1 mm in length) or cylindrical low-carbon steel electrodes (x 65, 10.0 mm in diameter and 10.0 mm in length, upper and lower surfaces were covered with tetrafluoroethylene (Teflon) disks) were used. The measuring cell was formed of two electrodes immersed in 300 ml of electrolyte. The electrolyte contained 822.5 MM of Na+, 12.78 mM of K+, 10.29 mM of Mg$^{2+}$, 33.66 mM of Ca$^{2+}$, 1.39 mM of Sr$^{2+}$, 3.20 mM of Ba$^{2+}$, 932.4 mM of Cl−, and 20 mM of HCO$^{3-}$ (pH 5.9) deoxygenated in advance with nitrogen. The electrolyte had a highly stable pH because carbonic acid and hydrogen carbonate salt formed a buffer system. To the electrolyte, was added 1–2% aqueous solution. Concentration of S group of the sample was 14.2 μmole/liter (generally, the concentration of sample was 2–5 ppm, that of the sodium salt of DMT-Pht was 4.1 ppm, and that of the sodium salt of DMT-Scc was 3.4 ppm). In the case of the addition of PEI, the concentration of PEI was set at 10 ppm.

The polarization resistance was determined by the calculation in accordance with the Ohm's law based on the change in voltage observed when current was passed between the electrodes. Since the corrosion speed is in inverse proportion to the polarization resistance, the ability to inhibit corrosion was calculated in accordance with the equation (1):

Ability to inhibit corrosion=(Rp sample−Rp cont)/Rp sample    (1)

In this equation, Rp cont denotes the Rp (Ω) before the addition of a corrosion inhibitor sample and Rp sample the Rp (Ω) after the addition of the corrosion inhibitor sample. In the examples and the comparative examples, the ability to inhibiting corrosion was indicated by multiplying the numerical value of the equation (1) by 100 and reporting the product in percent.

In Examples 1–6, the effect of the sulfidoamidocarboxylic acid alone was measured. Tables 1 and 2 show the results of the effect of polyamine so arranged as to facilitate comprehension. Examples 8, 9, and 10 represent cases of using polyamine and sulfidoamidocarboxylic acid in combination and consequently amounting to the addition of the salt of sulfidoamidocarboxylic acid with polyamine. Comparative Examples 1, 2, and 3 represent cases of using sulfidoamidocarboxylic acid alone and Comparative Examples 4 and 5 cases of using polyamine alone. When polyamine and sulfidoamidocarboxylic acid (salt) were used in combination, the effect of corrosion inhibition was accelerated prominently. The comparison of Example 8 with Comparative Examples 1 and 4, for example, reveals that the initial speed of manifestation was increased to about 2.4 times the original level. Likewise in Examples 9 and 10, the initial speed was increased to 1.2 to 1.6 times the original level (estimated on the basis of the sum of the increases of the initial polarization resistance observed in the relevant comparative examples in consequence of the addition of polyamine and sulfidoamidocarboxylic acid (salt)), respectively. It is evident that the manifestation speed of both polyamine and sulfidoamidocarboxylic acid in corrosion inhibition was high as compared with the case of adding the compounds independently of each other.

The entire disclosure of Japanese Patent Application Nos. 2000-131272 and 2000-380868 filed on Apr. 28, 2000 and Dec. 14, 2000 respectively including specification, claims and summary are incorporated herein by reference in its entirety.

What is claimed is:

1. A compound represented by the formula (I):

wherein CnHm and Cn'Hm' each denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to 2i +2−k −z, k for 2, and z for 1 or 2, and M represents a hydrogen atom or a metal atom or an ammonium.

2. A compound selected from the group consisting of DMT-succinamic acid, DMT-maleamic acid, DMT-phthalamic acid, DMT-trimellitamic acid, DMT-hexahydrophthalamic acid, and DMT-dodecenylsuccinamic acid, wherein DMT means dimethylthiazolidine residue.

3. A method for inhibiting corrosion of a metal material by adding a compound represented by the formula (I):

wherein CnHm and Cn'Hm' denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to 2i+2−k−z, k for an integer of 1–5, and z for an integer of 1–5, and M represents a hydrogen atom or a metal atom or an ammonium, into an aqueous medium in which the metal material exist.

4. A composition containing a polyamine having a number average molecular weight in the range of 595 to 7,000,000 or a salt thereof and a compound represented by the formula (I):

wherein CnHm and Cn'Hm' denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to 2i +2−k −z, k for an integer of 1–5, and z for an integer of 1–5, and M represents a hydrogen atom or a metal atom or an animonium.

5. A composition according to claim 4, an amount of the polyamine to the compound is in the weight range of 10:1–1:10.

6. A composition according to claim 4, wherein the compound is at least one member selected from the group consisting of DMT-succinamic acid, DMT-maleamic acid, DMT-phthalamic acid, DMT-trimellitamic acid, DMT-hexahydrophthalamic acid, and DMT-dodecenylsuccinamic acid, wherein DMT means dimethylthiazolidine residue.

7. A salt obtained by the reaction of a polyamine having a number average molecular weight in the range of 595 to 7,000,000 or a salt thereof with a compound represented by the formula (I):

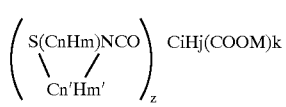
(I)

wherein CnHm and Cn'Hm' denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to $2i+2-k-z$, k for an integer of 1–5, and z for an integer of 1–5, and M represents a hydrogen atom or a metal atom or an ammonium.

8. A method for inhibiting corrosion of a metal material by adding into an aqueous medium in which the metal material exist a composition containing a polyamine or a salt thereof and a compound represented by the formula (I):

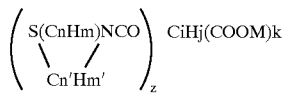
(I)

wherein CnHm and Cn'Hm' each denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to $2i+2-k-z$, k for an integer of 1–5, and z for an integer of 1–5, and M represents a hydrogen atom or a metal atom or an ammonium.

9. The method of claim 8, wherein the polyamine has a number average molecular weight in the range of 595 to 7,000,000.

10. A method for inhibiting corrosion of a metal material by adding into an aqueous medium in which the metal material exist a salt obtained by the reaction of a polyamine or a salt thereof with a compound represented by the formula (I):

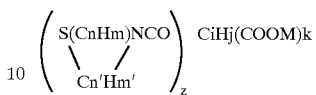
(I)

wherein CnHm and Cn'Hm' each denote independently a hydrocarbon chain, CiHj denotes a hydrocarbon chain, n stands for an integer of 1–12, m for an integer of 2 to 2n, n' for an integer of 1–15, m' for an integer of 2 to 2n', i for an integer of 2–20, j for an integer of 0 to $2i+2-k-z$, k for an integer of 1–5, and z for an integer of 1–5, and M represents a hydrogen atom or a metal atom or an ammonium.

11. The method of claim 10, wherein the polyamine has a number average molecular weight of 600 or higher.

12. A compound selected from the group consisting of a DMT-maleamic acid salt, a DMT-trimellitamic acid salt, DMT-pyromellitamic acid and a salt thereof, a DMT-hexahydrophthalamic acid salt, DMT-tetrahydrophthalamic acid and a salt thereof, MT-maleamic acid and a salt thereof, MT-trimellitamic acid and a salt thereof, MT-pyromellitamic acid, T-maleamic acid and a salt thereof, T-trimellitamic acid and a salt thereof, and T-pyromellitamic acid and a salt thereof, wherein DMT means dimethyl thiazolidine residue, MT means methylthiazolidine residue, and T means thiazolidine residue.

* * * * *